US00PP32571P2

(12) United States Plant Patent
Holtmaat

(10) Patent No.: US PP32,571 P2
(45) Date of Patent: Dec. 1, 2020

(54) ***RUDBECKIA* PLANT NAMED 'RUDBL242'**

(50) Latin Name: *Rudbeckia hirta*
Varietal Denomination: RUDBL242

(71) Applicant: Henricus Maria Joseph Holtmaat, Zuidwolde (NL)

(72) Inventor: Henricus Maria Joseph Holtmaat, Zuidwolde (NL)

(73) Assignee: NOVA PERENNE BV, Zuidwolde (NL)

( * ) Notice: Subject to any disclaimer, the term of this patent is extended or adjusted under 35 U.S.C. 154(b) by 0 days.

(21) Appl. No.: 16/873,157

(22) Filed: Feb. 15, 2020

(30) Foreign Application Priority Data

Jan. 6, 2020 (QZ) ..... PBR 2020/0004

(51) Int. Cl.
*A01H 5/02* (2018.01)
*A01H 6/14* (2018.01)

(52) U.S. Cl.
USPC ..... Plt./474
CPC ..... *A01H 6/14* (2018.05)

(58) Field of Classification Search
USPC ..... Plt./474
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Rudbeckia* plant named 'RUDBL242' that is characterized by its vigorous growth habit, its very floriferous blooming habit, its inflorescences that are large in size, and its inflorescences with disk florets that are dark brown in color and ray florets that are yellow in color with dark grey-purple bases.

2 Drawing Sheets

Botanical classification: *Rudbeckia hirta.*
Variety denomination: 'RUDBL242'.

CROSS REFERENCE TO RELATED APPLICATIONS

This application claims priority to European Community Plant Variety Office (CPVO) Plant Breeder's Rights Application No. 2020/0004 filed on Jan. 6, 2020 under 35 U.S.C. 119(f), the entire contents of which is incorporated by reference herein.

BACKGROUND OF THE INVENTION

The present invention relates to a new and distinct cultivar of *Rudbeckia hirta* and will hereafter by referred to by its cultivar name, 'RUDBL242'. The new cultivar is an herbaceous perennial grown for use as a landscape plant.

'RUDBL242' was derived from a breeding program conducted by the Inventor at a nursery in Zuidwolde, The Netherlands. The objective of the breeding program was to select new cultivars of *Rudbeckia* with floriferous blooming habits and compact plant habits.

'RUDBL242' was selected in July of 2018 by the Inventor from amongst seedlings in a trial field that had been planted with seed derived from open pollination of numerous unpatented and unnamed proprietary plants from the Inventor's breeding program in July 2017. The exact parentage is therefore unknown.

Asexual propagation of the new cultivar was first accomplished under the direction of the Inventor by tissue culture using meristematic tissue in Heerhugowaard, The Netherlands in March of 2019. Asexual propagation by tissue culture has determined that the characteristics of the new cultivar are stable and are reproduced true to type in successive generations.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to a website listing by AB-Cultivars (a company owned by the Inventor).

SUMMARY OF THE INVENTION

The following traits have been repeatedly observed and represent the characteristics of the new cultivar. These attributes in combination distinguish 'RUDBL242' as a unique cultivar of *Rudbeckia.*

1. 'RUDBL242' exhibits a vigorous growth habit.
2. 'RUDBL242' exhibits a very floriferous blooming habit.
3. 'RUDBL242' exhibits inflorescences that are large in size.
4. 'RUDBL242' exhibits inflorescences with disk florets that are dark brown in color and ray florets that are yellow in color with dark grey-purple bases.

'RUDBL242' can be compared to the *Rudbeckia* cultivars 'RUDHT37' and 'Kissing SmileyZ' (not patented). 'RUDHT37' is similar to 'RUDBL242' in having strong stems and a similar plant height. 'RUDHT37' differs from 'RUDBL242' in having a more narrow and less spreading plant habit and inflorescence with ray florets that are solid yellow in color. 'Kissing SmileyZ' is similar to 'RUDBL242' in inflorescence size and in foliage colors. 'Kissing SmileyZ' differs from 'RUDBL242' in having stronger stems and inflorescence disks that are green-yellow in color.

BRIEF DESCRIPTION OF THE DRAWINGS

The accompanying colored photographs illustrate the overall appearance and distinct characteristics of the new *Rudbeckia*. The photographs were taken of a 6-month-old plant of 'RUDBL242' as grown outdoors in a 17-cm container in Zuidwolde, The Netherlands.

The photograph in FIG. 1 is a side view of 'RUDBL242' in bloom.

Figure 1:
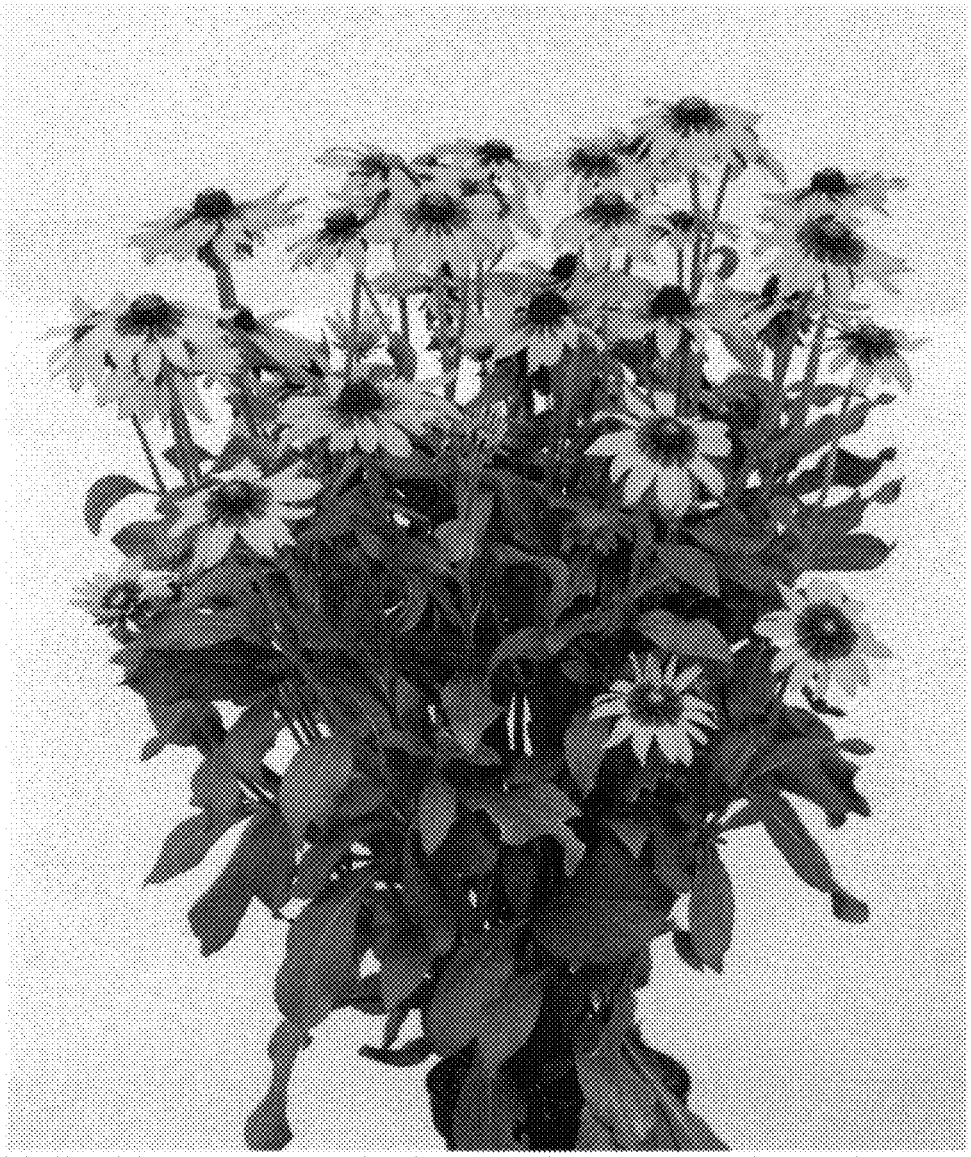
Figure 2:
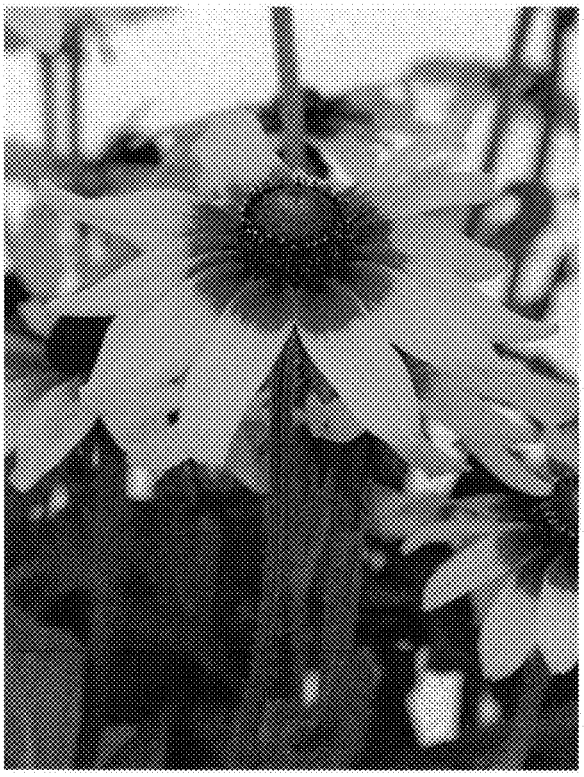

The photograph in FIG. 2 provides a close-up view of an inflorescence of 'RUDBL242'.

Figure 3:
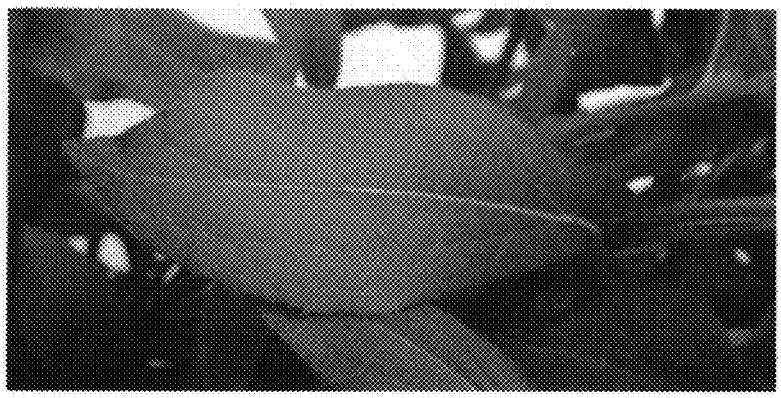

The photograph in FIG. 3 provides a close-up view of the foliage of 'RUDBL242'.

The colors in the photographs are as close as possible with the photographic and printing technology utilized and the color values cited in the detailed botanical description accurately describe the colors of the new *Rudbeckia*.

BOTANICAL DESCRIPTION OF THE PLANT

The following is a detailed description of 6-month-old plants of 'RUDBL242' as grown outdoors in 17-cm containers in Zuidwolde, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Average of 13 weeks from early summer to late summer in the Netherlands.

*Plant type.*—Perennial.

*Plant habit.*—Upright, compact.

*Plant shape.*—Obovate.

*Height and spread.*—Average of 55 cm in height from soil level to top of foliar plane and 69.9 cm in height from soil level to top of floral plane, 65 cm in diameter.

*Hardiness.*—At least in U.S.D.A. Zones 4 to 10.

*Diseases and pests.*—No susceptibility and resistance to diseases or pests has been observed.

*Root description.*—Fine and fibrous.

*Propagation.*—Tissue culture.

*Root development.*—An average of 3 weeks for root initiation with a young rooted plant produced in an average of 6 weeks.

*Growth rate and vigor.*—Vigorous.

Stem description:

*Stem shape.*—Moderately angled.

*Stem color.*—Young and mature stems; 144A to 144B, base N186C, 143A at the angles.

*Stem size.*—An average of 7 mm in diameter and an average of 31.1 cm in height.

*Stem surface.*—Moderately glossy and densely covered with strigose hairs an average of 2 mm in length and close to NN155D in color, young hairs N186C in color.

*Stem number.*—Average of 14 main stems, 3 lateral branches per main stem.

*Internode length.*—An average of 5.8 cm in length.

*Stem aspect.*—Main stems an average angle of 15° to vertical, lateral branches in an average angle of 25° to main stems.

*Branching.*—Freely branching from base with lateral stems, strong.

Foliage description:

*Leaf shape.*—Obovate to narrowly obovate.

*Leaf division.*—Simple.

*Leaf base.*—Long cuneate in lower leaves to short cuneate or truncate in upper leaves.

*Leaf apex.*—Bluntly acute to narrowly obtuse.

*Leaf venation.*—Pinnate, color upper surface 148D, color lower surface 146D.

*Leaf margins.*—Entire to un-deeply coarsely serrate, coarsely undulate.

*Leaf attachment.*—Sessile.

*Leaf arrangement.*—Alternate.

*Leaf size.*—Average of 16.1 cm in length and 5.8 cm in width.

*Leaf color.*—Young upper surface; 137C, young lower surface; 138B, mature upper surface; NN137C, mature lower surface; 147B.

*Leaf surface.*—Upper surface very slightly glossy, rough to touch, lower surface is matte, slightly rugose, rough to touch, both surfaces densely pubescent with short strigose hairs; an average of 1.5 mm in length and NN155D in color.

*Petioles.*—Leaves sessile.

Flower description:

*Type.*—Terminal capitulum, consisting of ray florets and disk florets.

*Capitulum number.*—1 per stem, up to 65 per plant.

*Lastingness of inflorescence.*—Average of 2 weeks, persistent.

*Capitulum size.*—Matures to about 3.8 cm in height and 11.4 cm in diameter, disk size is an average of 2.6 cm in diameter.

*Fragrance.*—None.

*Involucral bracts (phyllaries).*—Cuneate base, acute apex, oblanceolate to narrow oblong in shape, entire margins, average of 33 arranged in two rows, 2.1 cm in length and 5 mm in width, color; upper surface when fully open 137A, lower surface when fully open 138A to 138B, both surfaces and margins matte and densely covered with strigose hairs; an average of 1 mm in length and NN155D in color.

*Receptacle.*—Broad ovate in shape, an average of 1.4 cm in height, 1.2 in diameter, 157C in color.

*Buds.*—Globular in shape, immature ray florets pointed upward and curling inward, up to 2.5 cm in length and 3.7 cm in diameter, color; immature ray florets 8A, upper side of immature involucral bracts 137A, under side 138A, involucral bracts densely covered with strigose hairs; average 2 mm in length and NN155D in color, immature ray floret surface densely covered with strigose hairs; average of 1 mm in length and 158D in color.

*Peduncle.*—Strong, straight on top of main flowering stem, average of 20.3 cm in length and 4.5 mm in diameter, color; 144A to 144B, axially striped 143A, surface moderately glossy and densely covered with short strigose hairs; an average of 2 mm in length and NN155D in color.

*Ray florets.*—Average of 18 (varying between 17 and 19), rotate around the disc, oblong in shape, average of 5.4 cm in length and 1.7 cm in width, emarginate apex, cuneate base, entire margin, both surfaces are velvety, matte and glabrous, lower surface moderately covered with very short adpressed strigose hairs, average of 7 mm in length and 158D in color, held near horizontal, color; when opening upper surface; lower ¼$^{th}$ 187A, upper ¾$^{th}$ 17B, when opening lower surface; 13A, lower ⅓$^{rd}$ tinged 194B, when fully open upper and lower surface and veins; lower ¼th 183A, upper ¾th 14A, fading to; lower ¼$^{th}$ 175A, upper ¾$^{th}$ 17B, when fully open lower surface; 13A, changing to 148C at the base, fading to; 15B, changing to 146C at the base.

*Disk florets.*—Average of 600, tubular, 16 whorls arranged spirally on a conical receptacle, lower 90% fused into tube, upper 10% free, about 8 mm in length and 3 mm in width, free lobes have entire margins and are curled backwards, both surfaces glabrous and moderately glossy, color; when opening upper and lower surface; top 200B, mid-section 200A, tinged 187A, base 155A, when fully open upper and lower surface; top; between 200A and N186C, mid-section; in between 187A and 200B, base; 155A, spines; none, bracts; 1 at each disk floret, soft, flattened, an average of 7 mm in length and 1 mm in diameter, oblanceolate in shape, acute apex, narrow cuneate base, color; apex N186C, mid-section 155C, margins N186C, base 155C.

Reproductive organs:

*Gynoecium.*—Pistil; 1, 5 mm in length, style; 4 mm in length, color; 200A, mid-section 187A, base 155A, stigma; cleft, decurrent, 4 mm in diameter, 200A in color, ovary; NN155A in color.

*Androecium.*—Stamens; 5, filaments; 3 mm in length, 155A in color, anther; narrow oblong in shape, 2 mm in length, 0.5 mm in width, 200A to 203A in color, pollen; moderate in quantity and 17A in color.

*Fruit/seed.*—None observed.

It is claimed:

1. A new and distinct cultivar of *Rudbeckia* plant named 'RUDBL242' substantially as herein illustrated and described.

* * * * *